(12) United States Patent
Frank

(10) Patent No.: US 11,523,997 B2
(45) Date of Patent: Dec. 13, 2022

(54) METHOD OF PROVIDING CELIPROLOL THERAPY TO A PATIENT

(71) Applicant: Assistance Publique-Hôpitaux de Paris (AP-HP), Paris (FR)

(72) Inventor: Michael Frank, Gambais (FR)

(73) Assignee: ASSISTANCE PUBLIQUE-HOPITAUX DE PARIS (AP-HP), Paris (FR)

( * ) Notice: Subject to any disclaimer, the term of this patent is extended or adjusted under 35 U.S.C. 154(b) by 11 days.

(21) Appl. No.: 16/930,208

(22) Filed: Jul. 15, 2020

(65) Prior Publication Data
US 2021/0000770 A1    Jan. 7, 2021

Related U.S. Application Data

(63) Continuation of application No. 16/184,922, filed on Nov. 8, 2018, now abandoned.

(30) Foreign Application Priority Data

Dec. 21, 2017 (EP) ..................... 17306890

(51) Int. Cl.
*A61K 31/17* (2006.01)
*A61P 9/00* (2006.01)

(52) U.S. Cl.
CPC ............. *A61K 31/17* (2013.01); *A61P 9/00* (2018.01)

(58) Field of Classification Search
CPC .................................. A61K 31/17; A61P 9/00
See application file for complete search history.

(56) References Cited

U.S. PATENT DOCUMENTS

2019/0192455 A1    6/2019  Frank
2019/0192456 A1    6/2019  Frank

OTHER PUBLICATIONS

Co-pending U.S. Appl. No. 16/879,511, filed May 20, 2020.*
Co-pending U.S. Appl. No. 17/472,499, filed Sep. 10, 2021.*
Celiprolol hydrochloride 200 mg film coated Tablets, emc 2017, https://www.medicines.org.uk/emc/product/4338/smpc, XP-002785094. (6 pages).
Extended European Search Report for European Patent Application No. 17306890.9 dated Oct. 17, 2018. (8 pages).
Ong et al., "Effect of celiprolol on prevention of cardiovascular events in vascular Ehlers-Danlos syndrome: a prospective randomised, open, blinded-endpoints trial", Lancet 2010, vol. 376, pp. 1476-1484, XP27598350.
Baas et al., "Six uneventful pregnancy outcomes in an extended vascular Ehlers-Danlos syndrome family." American Journal of Medical Genetics Part A 2016, 173A, pp. 519-523, XP002784959.
Boutouyrie et al., "Increased carotid wall stress in vascular Ehlers-Danlos syndrome", Circulation 2004, 109(12):1530-1535, XP2784925.
European Society of Gynecology (ESG) et al., "ESC Guidelines on the management of cardiovascular diseases during pregnancy: The Task Force on the Management of Cardiovascular Diseases during Pregnancy of the European Society of Cardiology (ESC)", European Heart Journal 2011, vol. 32, No. 24, pp. 3147-3197, XP2784957.
Extended European Search Report for European Patent Application No. 17306888.3 dated Oct. 10, 2018. (9 pages).
Extended European Search Report for European Patent Application No. 17306889.1 dated Oct. 4, 2018. (9 pages).
Frank et al., "Vascular Ehlers-Danlos Syndrome: Long-Term Observational Study," Journal of the American College of Cardiology, 2019, vol. 13, No. 15, pp. 1948-1957.
Gok et al., "Spontaneous brachial pseudo-aneurysm in a 12-year-old with kyphoscoliosis-type Ehlers-Danlos Syndrome", European Journal of Vascular and Endovascular Surgery 2012, 44:482-484, XP002784926.
Nawarskas et al., "Celiprolol: A Unique Selective Adrenoceptor Modulator", Cardiology in Review, 2017, vol. 25, No. 5, pp. 247-253, XP9508130.
Rohrbach et al., "Phenotypic variability of the kyphoscoliotic type of Ehlers-Danlos syndrome (EDS VIA): clinical, molecular and biochemical delineation." Orphanet Journal of Rare Diseases 2011, 6:46, XP21104121. (9 pages).
Westhoff-Bleck et al., "Cardiovascular disorders in pregnancy: diagnosis and management." Best Practice & Research Clinical Obstetrics and Gynaecology 2013, vol. 27, No. 6, pp. 821-834, XP2784958.
Eguchi, Kazuo, "New Insight into Effects of β-Blockers on Arterial Functions," Pulse. 2015, 3:190-194. Japan.

\* cited by examiner

*Primary Examiner* — Irina Neagu
(74) *Attorney, Agent, or Firm* — Sheppard Mullin Richter & Hampton LLP

(57) ABSTRACT

The present disclosure relates to the field of treatment of an orphan disease, in particular treatment of vascular Ehlers-Danlos syndrome (vEDS). More specifically, the present disclosure relates to novel up-titration dosage regimens (e.g., escalating dosage regimens) effective for treating vEDS patients with celiprolol.

15 Claims, 7 Drawing Sheets

| Clinical Severity | Baseline | 2017 | Remained within group |
|---|---|---|---|
| Very low | 51,5 | 38,6 | 75 |
| Low | 21,2 | 18,9 | 71,4 |
| Medium | 22,7 | 27,2 | 70 |
| High | 4,5 | 15,1 | 100 |

METHOD OF PROVIDING CELIPROLOL THERAPY TO A PATIENT

CROSS-REFERENCE TO RELATED APPLICATION

This application is a continuation of U.S. application Ser. No. 16/184,922, filed on Nov. 8, 2018, which claims the benefit of European Patent Application No. 17306890.9 filed Dec. 21, 2017, the entire content of which is incorporated herein by reference.

FIELD

The present disclosure relates to the field of treatment of an orphan disease, in particular treatment of vascular Ehlers-Danlos syndrome (vEDS). More specifically, the present disclosure relates to novel up-titration dosage regimens (e.g., escalating dosage regimens) effective for treating vEDS patients with celiprolol.

BACKGROUND

Vascular Ehlers-Danlos syndrome (vEDS) is a rare genetic condition secondary to mutation within the COL3A1 gene. Typically, vEDS has an autosomal dominant inheritance. The most common COL3A1 variants result either in glycine substitutions within the triple helix encoding type III procollagen or in truncating splice-site variants. Both are responsible for a disruption of proper assembly of type III procollagen into type III collagen fibrils with a dominant negative effect. The amount of mature type III collagen is thus dramatically reduced, which in turn results in an important loss of mechanical strength of hollow organs, especially arteries and bowels. Clinically, vEDS is characterized by four major and nine minor diagnostic criteria (Beighton et al. (1998) Am J Med Genet, 77:31-37). Vascular EDS is typically clinically silent until the late teenage years. Acute and spontaneous organ complications start to occur during early adulthood and repeat at unpredictable time intervals. Arterial accidents, also referred to as arterial events, are the most common complications in vEDS (e.g., vascular ruptures, vascular dissections), followed by bowel perforations and respiratory accidents (e.g., pneumothorax).

Life expectancy is reduced in vEDS patients to a median of 51 years due in part to the morbidity associated with this disorder, especially morbidity associated with arterial accidents or events. Over the last ten years, awareness of the disease has significantly increased and patient management has improved, especially in reducing acute arterial accidents.

Medical intervention to improve vEDS patient outcome has made an important step with the publication of the results of the BBEST trial (Ong et al., (2010) Lancet, 376:1476-1484). In this trial, a final administration of 200 mg twice a day (BID) of celiprolol to patients with either a phenotype of vEDS, or with molecularly proven vEDS, showed a 35% reduction in morbidity and mortality over a 5-year follow-up. However, due to the fragility of vEDS patients, and the inability to determine effectiveness of treatment with celiprolol by a secondary measure such as blood pressure, in the BBEST trial, treatment was initiated with a daily dose of 100 mg of celiprolol. The BBEST trial disclosed a dose up-titration regimen for patients, wherein the patient received an initial daily dosage of 100 mg celiprolol for the first 6-months; then the dosage was increased (up-titrated) by an additional 100 mg celiprolol per day every 6-months, reaching a maximum daily dosage of 400 mg. Accordingly, reaching a maximum daily dosage of 400 mg (200 mg BID) was thus only achieved at 18 months. As a result, a very long up-titration period (e.g., long dose escalation period) of 18 months was necessary until the target dose was attained. This very long up-titration period was justified by the risk of adverse effects and of celiprolol intolerance. However, vEDS is a disease affecting young adults with a high risk of repeated and unpredictable arterial accidents (e.g., vascular ruptures, vascular dissections) who need optimal vascular protection as early as possible upon vEDS diagnosis, which is not compatible with an up-titration or dose escalation period of 18 months, as reported in the BBEST trial.

Thus there remains an unmet clinical need for improved treatment strategies and methods of treating a vEDS patient.

SUMMARY

The present disclosure provides improved treatment strategies and methods of administering higher doses of celiprolol to a vEDS patient in a manner that results in improved event-free survival and overall survival, eliminates or minimizes adverse events and celiprolol intolerance, by providing shorter up-titration and dose escalation periods of time.

The present disclosure provides, inter alia, improved, optimized dose escalation regimens and up-titration regimens for the administration of celiprolol to patients having vascular Ehlers-Danlos syndrome. The dose escalation and up-titration regimens of the present disclosure provide celiprolol, or a pharmaceutically acceptable salt thereof, to vEDS patients in an amount (e.g., an increasing amount) such that a dosage of at least 400 mg per day is reached within three months of initiating celiprolol treatment. The methods provided herein provide novel treatment regimens for the treatment of vEDS, resulting in improved overall survival and event-free survival.

In one embodiment, the present disclosure provides a method of providing or administering celiprolol therapy to a vEDS patient comprising providing or administering to the patient an initial daily dosage of celiprolol, or a pharmaceutically acceptable salt thereof, for the duration of a first period of time; followed by providing to the patient a second daily dosage of celiprolol, or a pharmaceutically acceptable salt thereof, for the duration of a second period of time; followed by providing to the patient a third daily dosage of celiprolol, or a pharmaceutically acceptable salt thereof, for the duration of a third period of time; and followed by providing to the patient a fourth daily dosage of celiprolol, or a pharmaceutically acceptable salt thereof. In some embodiments, the method further comprises providing to the patent a fifth daily dosage of celiprolol, or a pharmaceutically acceptable salt thereof. In some embodiments, the fourth daily dosage, or any daily dosage beyond the fourth daily dosage, is considered a maintenance dosage.

In some embodiments, the initial daily dosage is about 100 mg celiprolol or a pharmaceutically acceptable salt thereof. In some embodiments, the second daily dosage is about 200 mg celiprolol, or a pharmaceutically acceptable salt thereof. In some embodiments, the third daily dosage is about 300 mg celiprolol, or a pharmaceutically acceptable salt thereof. In some embodiments, the fourth daily dosage is about 400 mg celiprolol, or a pharmaceutically acceptable salt thereof. In other embodiments, the fifth daily dosage is greater than 400 mg celiprolol (e.g., 500 mg or 600 mg), or a pharmaceutically acceptable salt thereof.

In some embodiments, the first period of time is about one month, about 30 days, or about 28 days. In some embodiments, the second period of time is about one month, about 30 days, or about 28 days. In some embodiments, the third period of time is about one month, about 30 days, or about 28 days.

In one embodiment, the present disclosure provides a method of providing celiprolol therapy to a patient in need thereof in an initial dose escalation regimen, the method comprising providing or administering celiprolol, or a pharmaceutically acceptable salt thereof, to the patient at a daily dosage of about 100 mg for about one month; followed by providing or administering celiprolol, or a pharmaceutically acceptable salt thereof, to the patient at a daily dosage of about 200 mg for about one month; followed by providing or administering celiprolol, or a pharmaceutically acceptable salt thereof, to the patient at a daily dosage of about 300 mg for about one month; and following by providing or administering celiprolol, or a pharmaceutically acceptable salt thereof, to the patient at a dosage of about 400 mg.

In another embodiment, the present disclosure provides dose escalation regimen for providing celiprolol therapy to a patient for the treatment of vEDS, wherein the method comprises providing or administering celiprolol, or a pharmaceutically acceptable salt, to the patient at a first daily dosage of about 100 mg for about one month of the dose escalation regimen; followed by providing or administering celiprolol, or a pharmaceutically acceptable salt, to the patient at a second daily dosage of about 200 mg for one month of the dose escalation regimen; followed by providing or administering celiprolol, or a pharmaceutically acceptable salt, to the patient at a third daily dosage of about 300 mg for about one month of the dose escalation regimen; and followed by providing or administering celiprolol, or a pharmaceutically acceptable salt, to the patient at a fourth daily dosage of about 400 mg, wherein the patient is provided or administered celiprolol for the treatment of vascular Ehler-Danlos syndrome.

In one aspect, the disclosure provides methods for treating vascular Ehlers-Danlos syndrome. The methods include administering celiprolol, or a pharmaceutically acceptable salt thereof, to a patient in need thereof, wherein treatment begins with a titration period wherein celiprolol, or a pharmaceutically acceptable salt thereof, is administered at a dosage of about 100 mg once daily during one month and increased by about 100 mg/day every month over an about 3-month period to reach a dosage of about 400 mg per day. For example, the patient is administered celiprolol, or a pharmaceutically acceptable salt thereof, at a dosage of about 100 mg per day for about one month, at least a dosage of about 200 mg per day for about one month, at least a dosage of about 300 mg per day for about one month, and at least a dosage of about 360 mg, such as a dose of at least 400 mg (e.g., about 200 mg twice per day), from the end of the third month.

In one aspect, the disclosure provides a method of treating vascular Ehlers-Danlos syndrome in a patient in need thereof. This method includes administering an initial dosage of celiprolol, or a pharmaceutically acceptable salt thereof, of 100 mg per day to the patient and administering a subsequent dose of celiprolol, or a pharmaceutically acceptable salt thereof, of at least 400 mg per day (e.g., 200 mg twice per day) to the patient within 90 days of the initial dose. In some embodiments, a dosage of at least 200 mg per day is administered to the patient within 30 days of the initial dose. In some embodiments, a dosage of at least 300 mg per day is administered to the patient within 60 days of the initial dose.

In one aspect, the disclosure provides a method of treating vascular Ehlers-Danlos syndrome in a patient in need thereof. This method includes administering at least 400 mg per day (e.g., 200 mg twice per day) celiprolol, or a pharmaceutically acceptable salt thereof, to the patient within 120 days (e.g., within 90 days) of the initial dosage of celiprolol, or a pharmaceutically acceptable salt thereof. In some embodiments, the initial dosage of celiprolol, or a pharmaceutically acceptable salt thereof, is 100 mg per day.

In one embodiment, the present disclosure provides a method for treating vEDS in a patient in need thereof, the method comprising administering celiprolol, or a pharmaceutically acceptable salt thereof, to the patient at a first daily dosage of 100 mg for one month; followed by administering celiprolol, or a pharmaceutically acceptable salt thereof, to the patient a daily dosage of 200 mg for one month; followed by administering celiprolol, or a pharmaceutically acceptable salt, to the patient a daily dosage of 300 mg for one month; and followed by providing or administering celiprolol, or a pharmaceutically acceptable salt thereof, to the patient a daily dosage of 400 mg, thereby treating vEDS.

In one embodiment, the present disclosure provides for the use of celiprolol, or a pharmaceutically acceptable salt thereof, for treatment of vEDS, wherein celiprolol, or a pharmaceutically acceptable salt thereof, is administered to a patient having vEDS at a first daily dosage of 100 mg for 1 month, followed by a daily dose of 200 mg for 1 month, followed by a daily dose of 300 mg for 1 month, and followed by a daily dose of 400 mg.

In some embodiments, the dosage of celiprolol, or a pharmaceutically acceptable salt thereof, is reduced (e.g., reduced by 100 mg per day) if any signs of intolerance to the drug (e.g., swelling, fatigue, or flu-like symptoms) are experienced by the patient during up-titration or follow-up.

In some embodiments, the method further includes administering a dosage of at least 500 mg per day (e.g., at least 600 mg per day). In some embodiments, the dosage is increased to at least 500 mg per day after the three-month up-titration or dose escalation period.

In some embodiments, the initial daily dosage is about 91.25 mg celiprolol or an equivalent amount of a pharmaceutically acceptable salt thereof. In some embodiments, the second daily dosage is about 182.5 mg celiprolol, or an equivalent amount of a pharmaceutically acceptable salt thereof. In some embodiments, the third daily dosage is about 273.75 mg celiprolol, or an equivalent amount of a pharmaceutically acceptable salt thereof. In some embodiments, the fourth daily dosage is about 365 mg celiprolol, or an equivalent amount of a pharmaceutically acceptable salt thereof. In other embodiments, the fifth daily dosage is greater than 365 mg celiprolol (e.g., about 450 mg or about 550 mg), or an equivalent amount of a pharmaceutically acceptable salt thereof.

In some embodiments, the first period of time is about one month, about 30 days, or about 28 days. In some embodiments, the second period of time is about one month, about 30 days, or about 28 days. In some embodiments, the third period of time is about one month, about 30 days, or about 28 days.

In one embodiment, the present disclosure provides a method of providing celiprolol therapy to a patient in need thereof in an initial dose escalation regimen, the method comprising providing or administering celiprolol, or a pharmaceutically acceptable salt thereof, to the patient at a daily dosage of about 91.25 mg celiprolol for one month; followed by providing or administering celiprolol, or a pharmaceutically acceptable salt thereof, to the patient at a daily dosage of about 182.5 mg celiprolol for one month; followed by providing or administering celiprolol, or a pharmaceutically acceptable salt thereof, to the patient at a daily dosage of about 273.75 mg celiprolol for one month; and following by providing or administering celiprolol, or a pharmaceutically acceptable salt thereof, to the patient at a daily dosage of about 365 mg celiprolol.

In another embodiment, the present disclosure provides dose escalation regimen for providing celiprolol therapy to a patient for the treatment of vEDS, wherein the method comprises providing or administering celiprolol, or a pharmaceutically acceptable salt, to the patient at a first daily dosage of about 91.25 mg celiprolol for one month of the dose escalation regimen; followed by providing or administering celiprolol, or a pharmaceutically acceptable salt, to the patient at a second daily dosage of about 182.5 mg celiprolol for one month of the dose escalation regimen; followed by providing or administering celiprolol, or a pharmaceutically acceptable salt, to the patient at a third daily dosage of about 273.75 mg celiprolol for one month of the dose escalation regimen; and followed by providing or administering celiprolol, or a pharmaceutically acceptable salt, to the patient at a fourth daily dosage of about 365 mg celiprolol, wherein the patient is provided or administered celiprolol for the treatment of vascular Ehler-Danlos syndrome.

In one aspect, the disclosure provides methods for treating vascular Ehlers-Danlos syndrome. The methods include administering celiprolol, or a pharmaceutically acceptable salt thereof, to a patient in need thereof, wherein treatment begins with a titration period wherein celiprolol, or a pharmaceutically acceptable salt thereof, is administered at a dosage of about 91.25 mg celiprolol once daily during one month and increased by about 91.25 mg/day celiprolol every month over a 3-month period to reach a dosage of about 365 mg per day celiprolol. For example, the patient is administered celiprolol, or a pharmaceutically acceptable salt thereof, at a dosage of about 91.25 mg celiprolol per day for one month, at least a dosage of about 182.5 mg celiprolol per day for one month, at least a dosage of about 273.75 mg celiprolol per day for one month, and at least a dosage of about 330 mg celiprolol, such as a dose of at least about 365 mg (e.g., about 182.5 mg twice per day), from the end of the third month.

In one aspect, the disclosure provides a method of treating vascular Ehlers-Danlos syndrome in a patient in need thereof. This method includes administering an initial dosage of celiprolol, or a pharmaceutically acceptable salt thereof, of about 91.25 mg celiprolol per day to the patient and administering a subsequent dose of celiprolol, or a pharmaceutically acceptable salt thereof, of at least about 365 mg celiprolol per day (e.g., about 182.5 mg celiprolol twice per day) to the patient within 90 days of the initial dose. In some embodiments, a dosage of at least about 182.5 mg celiprolol per day is administered to the patient within 30 days of the initial dose. In some embodiments, a dosage of at least about 273.75 mg celiprolol per day is administered to the patient within 60 days of the initial dose.

In one aspect, the disclosure provides a method of treating vascular Ehlers-Danlos syndrome in a patient in need thereof. This method includes administering at least about 365 mg per day (e.g., about 182.5 mg twice per day) celiprolol, or an equivalent amount of a pharmaceutically acceptable salt thereof, to the patient within 120 days (e.g., within 90 days) of the initial dosage of celiprolol, or an equivalent amount of a pharmaceutically acceptable salt thereof. In some embodiments, the initial dosage of celiprolol is about 91.25 mg per day, or an equivalent amount of a pharmaceutically acceptable salt thereof.

In one embodiment, the present disclosure provides a method for treating vEDS in a patient in need thereof, the method comprising administering celiprolol, or a pharmaceutically acceptable salt thereof, to the patient at a first daily dosage of about 91.25 mg celiprolol for about one month; followed by administering celiprolol, or a pharmaceutically acceptable salt thereof, to the patient a second daily dosage of about 182.5 mg celiprolol for about one month; followed by administering celiprolol, or a pharmaceutically acceptable salt, to the patient a third daily dosage of about 273.75 mg celiprolol for about one month; and followed by providing or administering celiprolol, or a pharmaceutically acceptable salt thereof, to the patient a fourth daily dosage of about 365 mg celiprolol, thereby treating vEDS.

In one embodiment, the present disclosure provides for the use of celiprolol, or a pharmaceutically acceptable salt thereof, for treatment of vEDS, wherein celiprolol, or a pharmaceutically acceptable salt thereof, is administered to a patient having vEDS at a first daily dosage of about 91.25 mg celiprolol for about 1 month, followed by a second daily dose of about 182.5 mg celiprolol for about 1 month, followed by a third daily dose of about 273.75 mg celiprolol for about 1 month, and followed by a fourth daily dose of about 365 mg celiprolol.

In some embodiments, the dosage of celiprolol, or a pharmaceutically acceptable salt thereof, is reduced (e.g., reduced by about 91.25 mg celiprolol per day) if any signs of intolerance to the drug (e.g., swelling, fatigue, or flu-like symptoms) are experienced by the patient during up-titration or follow-up.

In some embodiments, the method further includes administering a dosage of at least about 456 mg per day (e.g., at least about 547.5 mg per day) celiprolol. In some embodiments, the dosage is increased to at least about 456 mg per day celiprolol after the three-month up-titration or dose escalation period.

In some embodiments, after the initial about three-month up-titration or dose escalation period, the patient is provided or administered a daily dosage of about 365 mg celiprolol or an equivalent amount of a pharmaceutically acceptable salt thereof for the treatment of vascular Ehler-Danlos syndrome for at least one year, two years, three years, four years, five years, five years and nine months or six years.

In some embodiments, the celiprolol or pharmaceutically acceptable salt thereof is celiprolol hydrochloride.

In some embodiments, the initial daily dosage is about 100 mg celiprolol hydrochloride. In some embodiments, the second daily dosage is about 200 mg celiprolol hydrochloride. In some embodiments, the third daily dosage is about 300 mg celiprolol hydrochloride. In some embodiments, the fourth daily dosage is about 400 mg celiprolol hydrochloride. In other embodiments, the fifth daily dosage is greater than 400 mg (e.g., about 500 mg or about 600 mg) celiprolol hydrochloride.

In some embodiments, the first period of time is about one month, about 30 days, or about 28 days. In some embodiments, the second period of time is about one month, about 30 days, or about 28 days. In some embodiments, the third period of time is about one month, about 30 days, or about 28 days.

In one embodiment, the present disclosure provides a method of providing celiprolol therapy to a patient in need thereof in a dose escalation regimen, the method comprising providing or administering celiprolol hydrochloride to the patient at a daily dosage of 100 mg for one month; followed by providing or administering celiprolol hydrochloride to the patient at a daily dosage of 200 mg for one month; followed by providing or administering celiprolol hydrochloride to the patient at a daily dosage of 300 mg for one month; and following by providing or administering celiprolol hydrochloride to the patient at a dosage of 400 mg.

In another embodiment, the present disclosure provides dose escalation regimen for providing celiprolol therapy to a patient for the treatment of vEDS, wherein the method comprises providing or administering celiprolol hydrochloride to the patient at a first daily dosage of about 100 mg (e g., once daily) for about one month of the dose escalation regimen; followed by providing or administering celiprolol hydrochloride to the patient at a second daily dosage of about 200 mg (e g., about 200 mg once daily or about 100 mg twice daily) for about one month of the dose escalation regimen; followed by providing or administering celiprolol hydrochloride to the patient at a third daily dosage of about 300 mg (e g., about 300 mg once daily, about 150 mg twice daily or about 100 mg thrice daily) for about one month of the dose escalation regimen; and followed by providing or administering celiprolol hydrochloride to the patient at a fourth daily dosage of about 400 mg (e g., about 400 mg once daily, about 200 mg twice daily, about 133 mg thrice daily or about 100 mg four times daily), wherein the patient is provided or administered celiprolol for the treatment of vascular Ehler-Danlos syndrome.

In one aspect, the disclosure provides methods for treating vascular Ehlers-Danlos syndrome. The methods include administering celiprolol hydrochloride to a patient in need thereof, wherein treatment begins with a titration period wherein celiprolol hydrochloride is administered at a dosage of 100 mg per day (e.g., once daily) during one month and increased by 100 mg/day every month over a 3-month period to reach a dosage of 400 mg per day. For example, the patient is administered celiprolol hydrochloride at a dosage of 100 mg per day for one month, at least a dosage of 200 mg per day for one month, at least a dosage of 300 mg per day for one month, and at least a dosage of 360 mg, such as a dose of at least 400 mg (e.g., 200 mg twice per day), from the end of the third month.

In one aspect, the disclosure provides a method of treating vascular Ehlers-Danlos syndrome in a patient in need thereof. This method includes administering an initial dosage of celiprolol hydrochloride of 100 mg per day (e.g., once daily) to the patient and administering a subsequent dose of celiprolol hydrochloride of at least 400 mg per day (e.g., 200 mg twice per day) to the patient within 90 days of the initial dose. In some embodiments, a dosage of at least 200 mg per day is administered to the patient within 30 days of the initial dose. In some embodiments, a dosage of at least 300 mg per day is administered to the patient within 60 days of the initial dose.

In one aspect, the disclosure provides a method of treating vascular Ehlers-Danlos syndrome in a patient in need thereof. This method includes administering at least 400 mg per day (e.g., 200 mg twice per day) celiprolol hydrochloride to the patient within 120 days (e.g., within 90 days) of the initial dosage of celiprolol hydrochloride. In some embodiments, the initial dosage of celiprolol hydrochloride is 100 mg per day.

In one embodiment, the present disclosure provides a method for treating vEDS in a patient in need thereof, the method comprising administering celiprolol hydrochloride to the patient at a first daily dosage of 100 mg for one month; followed by administering celiprolol hydrochloride to the patient a second daily dosage of 200 mg for one month; followed by administering celiprolol hydrochloride to the patient a third daily dosage of 300 mg for one month; and followed by administering celiprolol hydrochloride to the patient a fourth daily dosage of 400 mg, thereby treating vEDS.

In one embodiment, the present disclosure provides for the use of celiprolol hydrochloride for treatment of vEDS, wherein celiprolol hydrochloride is administered to a patient having vEDS at a first daily dosage of about 100 mg for about 1 month, followed by a second daily dose of about 200 mg for about 1 month, followed by a third daily dose of about 300 mg for about 1 month, and followed by a fourth daily dose of about 400 mg.

In some embodiments, after the initial about three-month up-titration or dose escalation period, the patient is provided or administered a fourth daily dosage of about 400 mg celiprolol hydrochloride for the treatment of vascular Ehler-Danlos syndrome for at least one year, two years, three years, four years, five years, five years and nine months or six years.

In some embodiments, the dosage of celiprolol hydrochloride is reduced (e.g., reduced by about 100 mg per day) if any signs of intolerance to the drug (e.g., swelling, fatigue, or flu-like symptoms) are experienced by the patient during up-titration or follow-up.

In some embodiments, the method further includes administering a dosage of at least 500 mg per day (e.g., at least 600 mg per day) celiprolol hydrochloride. In some embodiments, the dosage is increased to at least 500 mg per day after the three-month up-titration or dose escalation period.

In some embodiments, the patient is a human patient. In some embodiments, the patient is 15-years old or older. In some embodiments, the patient is an adult patient. In some embodiments, the patient is a pediatric patient.

In some embodiments, the method is initiated as soon as (or soon after) vEDS is diagnosed. In some embodiments, the method is initiated when the patient is 15 years old.

In some embodiments, the patient is diagnosed based on a phenotype of vEDS, or based on a molecular test vEDS (e.g., the patient is determined to have vEDS based on one or more genetic tests such as a test that determines that the patient has a glycine substitution within the triple helix or a splice-site variant).

In some embodiments, the patient has a COL3A1 mutation. In some embodiments, the patient has a glycine substitution within the triple helix or a splice-site variant. In some embodiments, the patient has a missense substitutions for glycine in the repeating (Gly-X-Y)n sequence of the collagen triple helix, or and splice site variants that lead to in-phase exon-skipping. In some embodiments, the patient has a glycine substitution within the triple helix (Group I). In some embodiments, the patient has a splice-site variant, in-frame insertions-deletion or duplication (Group II). In some embodiments, the patient has a variant leading to haplo-insufficiency (Group III).

In some embodiments, the patient has previously had an acute vEDS-related event (e.g., an arterial event such as a rupture or dissection, an intestinal or uterine rupture) prior to the initial dose of celiprolol, or a pharmaceutically acceptable salt thereof.

In some embodiments, methods of the present disclosure as provided herein result in fewer adverse vascular events (e.g., an arterial rupture or dissection) in a vEDS patient than prior methods for providing celiprolol for the treatment of vEDS, such method including up titrating to a dose of at least 400 mg per day over 18 months. In some embodiments, methods of the present disclosure provide greater overall survival (e.g., over a five year follow up period) compared to the corresponding method which includes up titrating to a dose of at least 400 mg per day over 18 months.

BRIEF DESCRIPTION OF THE DRAWINGS

Kaplan-Meier survival analysis of n=144 vascular EDS patients treated with celiprolol.

Kaplan-Meier survival analysis of patients with Glycine missense variants and splice-site variants, deletions, insertions and duplications (Groups I and II; n=132 patients), according to celiprolol treatment.

DETAILED DESCRIPTION

Figure 1:
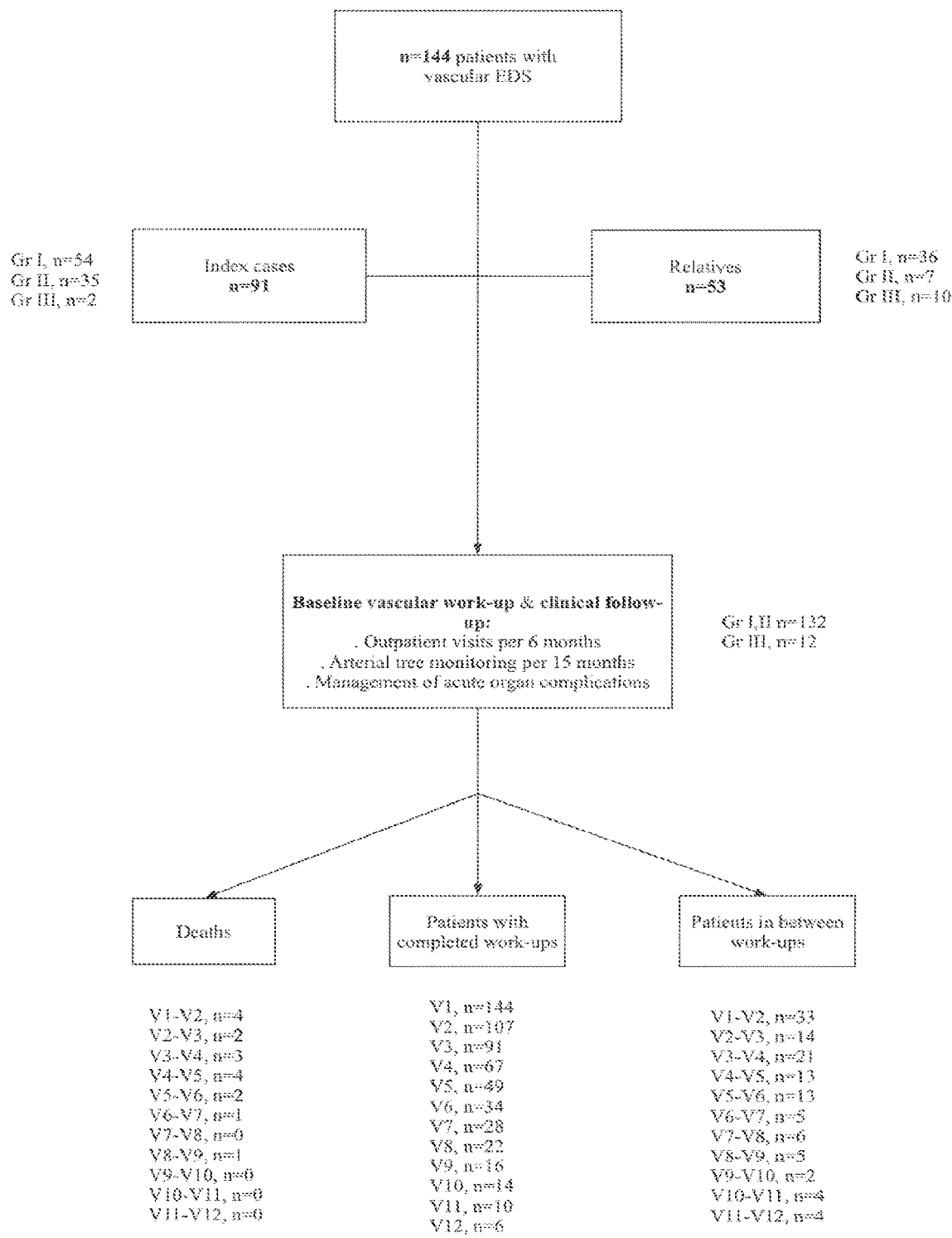
FIG. 1: Patient flowchart. Abbreviations: EDS: Ehlers-Danlos syndrome; Gr I: Group I (Glycine missense); Gr II: Group II (splice-site variants, insertions/deletions, duplications), Gr III: Group III (haploinsufficiency); V: follow-up visit with vascular work-up.

The present disclosure provides a method of providing celiprolol therapy to a patient with vEDS, wherein the method is associated with an escalating dosage regimen that mitigates adverse events and intolerance associated with the use of celiprolol, as well as providing better overall survival and event-free survival, and better matches the development of tolerance to potentially adverse effects of the drug with increases in the dosage. Unlike the use of celiprolol for the treatment of hypertension, wherein dosage titration and dosage effectiveness can be monitored by measuring blood pressure changes, the fragility of vEDS patients, and the inability to determine effectiveness of treatment with celiprolol by a secondary measure such as blood pressure, has led to a lack of physiological guidelines for appropriate up-titration and dose escalation strategies for this patient population. The present disclosure addresses this with novel up-titration and dose escalation methods for the effective treatment of vEDS.

In one embodiment of the present disclosure, a method is provided for providing or administering celiprolol therapy to a patient, the method comprising providing or administering an initial daily dosage of celiprolol (or a pharmaceutically acceptable salt thereof) to the patient for the duration of a first period of time; followed by providing or administering a second daily dosage of celiprolol (or a pharmaceutically acceptable salt thereof) to the patient for a second period of time; followed by providing or administering a third daily dosage of celiprolol (or a pharmaceutically acceptable salt thereof) to the patient for a third period of time; and followed by providing or administering a fourth daily dosage of celiprolol (or a pharmaceutically acceptable salt thereof) to the patient thereafter. The longer dose escalation periods reported previously are less than optimal for vEDS patient benefit resulting from the delay in administering a full therapeutic dosage of 18 months.

In the dose escalation regimen described herein, the first daily dosage is about 91.25 mg (e.g., about 91.25 mg once daily) celiprolol, or an equivalent amount of a pharmaceutically acceptable salt thereof, during the initial month, the initial 30 days, or the initial 28 days; the second daily dosage is about 182.5 mg (e.g., about 182.5 mg once daily, about 91.25 mg twice-daily) celiprolol, or an equivalent amount of a pharmaceutically acceptable salt thereof, during the second month, the second 30 days, or the second 28 days; the third daily dosage is about 273.75 mg (e.g., about 273.75 mg once daily, about 136.88 mg twice daily, about 91.25 mg thrice daily) celiprolol, or an equivalent amount of a pharmaceutically acceptable salt thereof, during the third month; and the fourth daily dosage is about 365 mg daily (e.g., about 365 mg once daily, about 182.5 mg twice daily) celiprolol, or an equivalent amount of a pharmaceutically acceptable salt thereof. The method of the present disclosure can further comprise additional steps after the three-month dose escalation/up-titration period, to further increase the daily dose of celiprolol administered to the patient. According to a particular embodiment, one or two additional dosage increases are performed after the three-month dose escalation/up-titration period, to reach a daily dosage of greater than 365 mg, such as for example, about 500 mg or about 600 mg of celiprolol or an equivalent amount of a pharmaceutically acceptable salt thereof. An equivalent amount of a pharmaceutically acceptable salt of celiprolol is the weight amount of the salt that provides the stated amount of celiprolol. For example, 200 mg of the HCl salt of celiprolol (celiprolol hydrochloride) provides and is equivalent to 182.5 mg of celiprolol.

In some embodiments, provided is celiprolol or a pharmaceutically acceptable salt thereof for use in treating vascular Ehlers-Danlos syndrome in a patient, wherein treatment begins with 80 to 110 mg (e.g., about 91.25 mg) daily celiprolol or an equivalent amount of a pharmaceutically acceptable salt of celiprolol and increases to 300 to 440 mg (e.g., about 365 mg) daily celiprolol or an equivalent amount of a pharmaceutically acceptable salt of celiprolol within six months. In some embodiments, provided is a method for treating vascular Ehlers-Danlos syndrome, comprising administering to a patient in need thereof a 80 to 110 mg (e.g., about 91.25 mg) daily dose of celiprolol or an equivalent amount of a pharmaceutically acceptable salt of celiprolol and increasing the daily dose to 300 to 440 mg (e.g., about 365 mg) within six months. In some embodiments, at least a 80 to 110 mg daily (e.g., about 91.25 mg) dose increase is made within two months. In some embodiments, at least a 170 to 210 mg (e.g., about 182.5 mg) daily dose increase is made within four months. In some embodiments, at least a 260 to 310 mg (e.g., about 273.75 mg) daily dose increase is made within six months. In some embodiments, at least a 260 to 310 mg (e.g., about 273.75 mg) daily dose increase is made within four months.

In some embodiments, provided is celiprolol hydrochloride for use in treating vascular Ehlers-Danlos syndrome in a patient, wherein treatment with celiprolol hydrochloride begins with 90 to 110 mg (e.g., about 100 mg) daily and increases to 360 to 440 mg (e.g., about 400 mg) daily within six months. In some embodiments, provided is a method for treating vascular Ehlers-Danlos syndrome, comprising administering to a patient in need thereof a 90 to 110 mg (e.g., about 100 mg) daily dose of celiprolol hydrochloride and increasing the daily dose to 360 to 440 mg (e.g., about 400 mg) within six months. In some embodiments, at least a 90 to 110 mg (e.g., about 100 mg) daily dose increase is made within two months. In some embodiments, at least a 180 to 220 mg (e.g., about 200 mg) daily dose increase is made within four months. In some embodiments, at least a 270 to 330 mg (e.g., about 300 mg) daily dose increase is made within six months. In some embodiments, at least a 270 to 330 mg (e.g., about 300 mg) daily dose increase is made within four months.

In the dose escalation regimen described herein, the first daily dosage is about 100 mg during the initial month, the initial 30 days, or the initial 28 days; the second daily dosage is about 200 mg (e.g., 200 mg once daily, 100 mg twice-daily) during the second month, the second 30 days, or the second 28 days; the third daily dosage is about 300 mg (e.g., 300 mg once daily, 150 mg twice daily, 100 mg thrice daily) during the third month; and the fourth daily dosage is about 400 mg daily (e.g., 400 mg once daily, 200 mg twice daily). The method of the present disclosure can further comprise additional steps after the three-month dose escalation/up-titration period, to further increase the daily dose of celiprolol administered to the patient. According to a particular embodiment, one or two additional dosage increases are performed after the three-month dose escalation/up-titration period, to reach a daily dosage of greater than 400 mg, such as for example, 500 mg or 600 mg of celiprolol.

In the dose escalation regimen described herein, the first daily dosage is about 100 mg (e.g., about 100 mg once daily) celiprolol hydrochloride during the initial month, the initial 30 days, or the initial 28 days; the second daily dosage is about 200 mg (e.g., about 200 mg once daily, about 100 mg twice-daily) celiprolol hydrochloride during the second month, the second 30 days, or the second 28 days; the third daily dosage is about 300 mg (e.g., about 300 mg once daily, about 150 mg twice daily, about 100 mg thrice daily) celiprolol hydrochloride during the third month; and the fourth daily dosage is about 400 mg daily (e.g., about 400 mg once daily, about 200 mg twice daily) celiprolol hydrochloride. The method of the present disclosure can further comprise additional steps after the three-month dose escalation/up-titration period, to further increase the daily dose of celiprolol administered to the patient. According to a particular embodiment, one or two additional dosage increases are performed after the three-month dose escalation/up-titration period, to reach a daily dosage of greater than 400 mg, such as for example, about 500 mg or about 600 mg of celiprolol hydrochloride.

Each period of time associated with a particular daily dosage is about one month. In some embodiments, the period of time associated with a particular dosage during the up-titration or dose escalation is about one month, about 30 days, or about 28 days.

Although the present disclosure exemplifies dose escalation and up-titration regimens having particular dosage increases over time, the present disclosure further contemplates additional dose escalation and up-titration steps in the same amount of time, such that the daily dosage escalates in smaller steps and more frequently. Indeed, if desired, each dosage for a particular period of time can be incrementally larger than the previous dosage, or the dosage can escalate, for example, every week, every 2-weeks, every 3-weeks.

In certain embodiments, the daily dosage of celiprolol is once daily. In other embodiments, the daily dosage of celiprolol is twice daily. In yet other embodiments, the daily dosage is thrice daily (three oral administrations daily).

According to one embodiment, the present disclosure pertains to a method of treating vascular Ehlers-Danlos syndrome, comprising administering celiprolol to a patient in need thereof, wherein treatment begins with a titration period wherein celiprolol, or a pharmaceutically acceptable salt thereof, is administered at a dosage of 100 mg daily during one month and increased by steps of 100 mg/day every month over a 3-month period to reach a dosage of 400 mg per day.

According to one embodiment, the present disclosure pertains to a method of treating vascular Ehlers-Danlos syndrome, comprising administering celiprolol to a patient in need thereof, wherein treatment begins with a titration period wherein celiprolol, or a pharmaceutically acceptable salt thereof, is administered at a dosage of 91.25 mg daily during one month and increased by steps of 91.25 mg/day every month over a 3-month period to reach a dosage of 91.25 mg per day of celiprolol.

As used herein, the term "comprise" or "include" is intended to mean that the compositions and methods include the recited elements, but not excluding others. "Consist essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consist of" shall mean excluding more than trace amount of other ingredients and substantial method steps recited. Embodiments defined by each of these transition terms are within the scope of this disclosure.

The term "about" when used before a numerical value indicates that the value may vary within reasonable range, such as ±10%, ±5%, and ±1%. The expression "about x" includes the value "x."

The singular forms "a" and "the" include plural references unless the context clearly dictates otherwise. Thus, e.g., reference to "the mutation" includes a plurality of mutations.

As used herein, the terms "treat", "treatment" and "treating" refer to any reduction of one or more symptom(s) associated with vascular EDS, such as, for example, a reduction of the occurrence and/or severity of cardiovascular accidents or events, and/or an increase in survival that results from the administration of celiprolol alone or combined with one or more other therapies.

Celiprolol (brand names Cardem®, Selectol®, Celipres®, Celipro®, Celol®, Cordiax®, Dilanorm®, Edsivo™) is a medication in the class of beta-blockers that is unique from others in its class in both its pharmacology and clinical applications. Its chemical formula is N'-(3-Acetyl-4-(3-((1,1-dimethylethyl)amino)-2-hydroxypropoxy)phenyl)-N,N-diethylurea, its CAS number is 56980-93-9 and Drug Bank number is DB04846.

According to an embodiment of the present disclosure, celiprolol is administered at a dose of 100 mg twice a day during the second month of treatment.

When performing any of the above methods of the present disclosure, signs of celiprolol intolerance can appear, especially during the titration period. Most often, intolerance leads to excessive fatigue. According to the present disclosure, the dose of celiprolol is reduced in case of signs of intolerance during up-titration or dose escalation, or during any follow-up. According to a particular embodiment, the dose reduction is a reduction of 100 mg/day (for example, a patient showing signs of intolerance at a daily dose of 400 mg/day will be given a reduced dose of 300 mg/day, etc.). According to a particular embodiment, the dose reduction is a reduction of about 91.25 mg/day (for example, a patient showing signs of intolerance at a daily dose of about 365 mg/day will be given a reduced dose of about 273.75 mg/day, etc.) celiprolol or an equivalent amount of a pharmaceutically acceptable salt thereof, for example, the dose reduction is a reduction of about 100 mg/day (for example, a patient showing signs of intolerance at a daily dose of about 400 mg/day will be given a reduced dose of 300 mg/day, etc.) celiprolol hydrochloride.

The inventors demonstrated that optimal effects of celiprolol for preventing cardiovascular accidents in vEDS patients are obtained in patients who take at least 360 mg/day of celiprolol. According to an embodiment of the present disclosure, celiprolol is thus administered at a dose at or above 360 mg/day at the end of the titration period.

According to an embodiment of the above method, illustrated in the experimental part below, celiprolol is administered at a dose of 200 mg twice a day at the end of the three-month titration period.

Optionally, the method of the present disclosure can further comprise additional steps after the three-month titration period, to further increase the dose of celiprolol administered to the patient. According to a particular embodiment, one or two additional dose increases are performed after the three-month titration period, to reach a daily dose of 500 mg or 600 mg of celiprolol. Situations that may justify such increases are acute arterial complications, uncontrolled recurrence of arterial complications within the same hospitalization, or patient stabilization after acute arterial complication(s).

As mentioned above, vascular EDS is typically clinically silent until the late teenage years. However, in order to better prevent the risk of arterial accidents or events (e.g., vascular ruptures, vascular dissections), bowel perforations, and/or respiratory accidents (pneumothorax) in late teenagers and in young adults, it is preferable to initiate the treatment as soon as possible upon diagnosis of vEDS, e.g., when the patient is 10-years old or older. Hence, according to an embodiment of the method of the disclosure, the treatment is initiated (i) upon vascular EDS diagnosis, if the patient is 10 or older, or (ii) when the patient is 10 years old, if vEDS has been previously diagnosed, or (iii) upon vascular EDS diagnosis, if the patient is less than 10 with an history of arterial event.

In some embodiments, celiprolol is administered in a pharmaceutical composition comprising celiprolol or a pharmaceutically acceptable salt thereof, and one or more pharmaceutically acceptable excipients. In some embodiments, the pharmaceutical composition is for oral administration. In some embodiments, the pharmaceutical composition is a tablet formulation, such as a film coated tablet. In some embodiments, the pharmaceutical composition is an immediate release formulation, such as an immediate release tablet formulation. In some embodiments, each tablet comprises about 182.5 mg celiprolol or about 200 mg of celiprolol hydrochloride.

In some embodiments, the starting dose of celiprolol administered to the patient is a ½ tablet (91.25 mg) once daily, which is titrated up in ½ tablet increments each month to a total dose of 2 tablets (365 mg) a day. In some embodiments, the daily dose between a ½ tablet and 2 tablets may be adjusted based on patient tolerance. In some embodiments, the daily dose can be given once per day or divided into twice a day dosing based on patient tolerance. For ½ tablet dose, the tablet can be split into equal parts using a tablet splitter.

In some embodiments, celiprolol is not administered within one hour of a meal. In some embodiments, celiprolol is not administered 1 hour before, or 2 hours after a meal.

In some embodiments, celiprolol is not co-administered with itraconazole, grapefruit juice, orange juice, chlorthalidone, hydrochlorothiazide, theophylline, or rifampicin. In some embodiments, celiprolol is not co-administered with a substrate of MATE1, MATE2-K, BCRP, or P-gp transporter. In some embodiments, celiprolol is not co-administered with calcium channel blockers, such as phenylalkylamine and benzothiazepine, hypotensive agents, or oral antidiabetic (hypoglycemics) drugs. In some embodiments, when co-administered with one or more of the agents, such as itraconazole, the dosage of celiprolol is reduced.

In some embodiments, celiprolol is not co-administered with general anesthesia. In some embodiments, anesthesia is not administered within about 24 hours of the last celiprolol dose. In some embodiments, anesthesia is not administered within about 48 hours of the last celiprolol dose.

In some embodiments, celiprolol is not administered to a patient having one or more of the following conditions: cardiogenic shock, decompensated cardiac failure, sick-sinus syndrome, heart block greater than first degree, severe bradycardia, severe renal impairment with creatinine clearance less than about 15 mL/minute, hypotension, or hypersensitivity to celiprolol.

In some embodiments, when treatment with celiprolol is discontinued, it is discontinued after gradually reducing the dosage over a period of at least one week, such as one to two weeks.

In some embodiments, provided is celiprolol hydrochloride for use in treating vascular Ehlers-Danlos syndrome in a patient that is receiving a 360 to 440 mg daily dose of celiprolol hydrochloride and having a need to cease the treatment, wherein the daily dose of celiprolol hydrochloride is reduced for no more than about 100 mg a day. In some embodiments, provided is method for ceasing the treatment of celiprolol hydrochloride in a patient that is receiving a 360 to 440 mg daily dose of celiprolol hydrochloride and having a need to cease the treatment, comprising reducing the daily dose of celiprolol hydrochloride for no more than about 100 mg a day. In some embodiments, the reduction continues for at least 5 days. In some embodiments, the reduction continues for at least 7 days. In some embodiments, the reduction continues for at least 10 days.

In some embodiments, provided is

1. A method of treating vascular Ehlers-Danlos syndrome, comprising administering celiprolol, or a pharmaceutically acceptable salt thereof, to a patient in need thereof, wherein treatment begins with a titration period wherein celiprolol, or a pharmaceutically acceptable salt thereof, is administered at a dose of 100 mg once daily during one month and increased by 100 mg/day every month over a 3-month period to reach a dose of 400 mg per day.

2. The method of 1 above, wherein during the second month, celiprolol, or a pharmaceutically acceptable salt thereof, is administered at a dose of 100 mg twice a day.

3. The method of 1 or 2 above, wherein in case of signs of intolerance during up-titration or follow-up, the dose of celiprolol, or a pharmaceutically acceptable salt thereof, is reduced.

4. The method of 3 above, wherein the daily dose of celiprolol, or a pharmaceutically acceptable salt thereof, is reduced by 100 mg.

5. The method of any one 1-4 above, wherein at the end of the titration period, celiprolol, or a pharmaceutically acceptable salt thereof, is administered at a dose superior to 360 mg/day.

6. The method of any one 1-5 above, wherein at the end of the titration period, celiprolol, or a pharmaceutically acceptable salt thereof, is administered at a dose of 200 mg twice a day.

7. The method of any one 1-6 above, wherein after the three-month titration period, one or two additional dose increases are performed to reach a daily dose of 500 mg or 600 mg.

8. The method of any one 1-7 above, wherein the patient is 15-years old or older.

9. The method of any one 1-7 above, wherein the treatment is initiated as soon as vascular EDS is diagnosed, or when the patient is 10 years old.

10. A method for treating vascular Ehlers-Danlos syndrome, comprising administering to a patient in need thereof a 90 to 110 mg daily dose of celiprolol hydrochloride and increasing the daily dose to 360 to 440 mg within six months.

11. A method of treating vascular Ehlers-Danlos syndrome, comprising administering celiprolol hydrochloride to a patient in need thereof, wherein the treatment begins with a titration period wherein celiprolol hydrochloride is administered at a dose of about 100 mg per day during about one month and increased by about 100 mg/day every month over an about 3-month period to reach a dose of about 400 mg per day.

12. The method of 11 above, wherein during the second month, celiprolol hydrochloride is administered at a dose of about 100 mg twice per day.

13. The method of 11 or 12 above, wherein in case of signs of intolerance during up-titration or follow-up, the dose of celiprolol hydrochloride is reduced.

14. The method of 13 above, wherein the daily dose of celiprolol hydrochloride is reduced by about 100 mg.

15. The method of any one of 11-14 above, wherein at the end of the titration period, celiprolol hydrochloride is administered at a dose superior to 360 mg/day.

16. The method of any one of 11-15 above, wherein at the end of the titration period, celiprolol hydrochloride is administered at a dose of about 400 mg per day.

17. The method of any one of 11-16 above, wherein after the three-month titration period, one or two additional dose increases are performed to reach a daily dose of about 500 mg or about 600 mg.

18. The method of any one of 11-17 above, wherein the patient is 15-years old or older.

19. The method of any one of 11-17 above, wherein the treatment is initiated as soon as vascular EDS is diagnosed, or when the patient is 10 years old.

20. A method for ceasing the treatment of celiprolol hydrochloride in a patient that is receiving a 360 to 440 mg daily dose of celiprolol hydrochloride and having a need to cease the treatment, comprising reducing the daily dose of celiprolol hydrochloride for no more than about 100 mg a day.

21. Celiprolol or a pharmaceutically acceptable salt thereof, for use in treating vascular Ehlers-Danlos syndrome, wherein treatment with celiprolol or a pharmaceutically acceptable salt thereof begins with a titration period during which celiprolol or a pharmaceutically acceptable salt thereof is administered at a dose of 100 mg once daily during one month and increased by 100 mg/day every month over a 3-month period to reach a dose of 400 mg per day.

22. Celiprolol or a pharmaceutically acceptable salt thereof, for the use of 21 above, wherein during the second month, celiprolol or a pharmaceutically acceptable salt thereof is administered at a dose of 100 mg twice a day.

23. Celiprolol or a pharmaceutically acceptable salt thereof, for the use of 21 or 22 above, wherein in case of signs of intolerance during up-titration or follow-up, the dose of celiprolol, or a pharmaceutically acceptable salt thereof, is reduced.

24. Celiprolol or a pharmaceutically acceptable salt thereof, for the use of 23 above, wherein the daily dose of celiprolol or a pharmaceutically acceptable salt thereof is reduced by 100 mg.

25. Celiprolol or a pharmaceutically acceptable salt thereof, for the use of any of 21 to 24 above, wherein at the end of the titration period, celiprolol or a pharmaceutically acceptable salt thereof is administered at a dose superior to 360 mg/day.

26. Celiprolol or a pharmaceutically acceptable salt thereof, for the use of any of 21 to 25 above, wherein at the end of the titration period, celiprolol or a pharmaceutically acceptable salt thereof is administered at a dose of 200 mg twice a day.

27. Celiprolol or a pharmaceutically acceptable salt thereof, for the use of any of 21 to 26 above, wherein after the three-month titration period, one or two additional dose increases are performed to reach a daily dose of 500 mg or 600 mg.

28. Celiprolol or a pharmaceutically acceptable salt thereof, for the use of any of 21 to 27 above, wherein the patient is 15-years old or older.

29. Celiprolol or a pharmaceutically acceptable salt thereof, for the use of any of 21 to 28 above, wherein treatment with celiprolol or a pharmaceutically acceptable salt thereof is initiated as soon as vascular EDS is diagnosed, or when the patient is 10 years old.

30. Celiprolol hydrochloride for use in treating vascular Ehlers-Danlos syndrome in a patient, wherein treatment with celiprolol hydrochloride begins with 90 to 110 mg daily and increases to 360 to 440 mg daily within six months.

31. Celiprolol hydrochloride for use of 30 above, wherein at least a 90 to 110 mg daily dose increase is made within two months.

32. Celiprolol hydrochloride for use of 30 or 31 above, wherein at least a 180 to 220 mg daily dose increase is made within four months.

33. Celiprolol hydrochloride for use of any one of 30 to 32 above, wherein at least a 270-330 mg daily dose increase is made within six months.

34. Celiprolol hydrochloride for use of any one of 30 to 33 above, wherein at least a 270-330 mg daily dose increase is made within four months.

35. Celiprolol hydrochloride for use in treating vascular Ehlers-Danlos syndrome in a patient, wherein treatment with celiprolol hydrochloride begins with a titration period during which celiprolol hydrochloride is administered at a dose of about 100 mg per day during one month and increased by 100 mg/day every month over an about 3-month period to reach a dose of about 400 mg per day.

36. Celiprolol hydrochloride for the use of 35 above, wherein during the second month, celiprolol hydrochloride is administered at a dose of about 200 mg per day.

37. Celiprolol hydrochloride for the use of 35 or 36 above, wherein in case of signs of intolerance during up-titration or follow-up, the dose of celiprolol hydrochloride is reduced.

38. Celiprolol hydrochloride for the use of 37 above, wherein the daily dose of celiprolol hydrochloride is reduced by about 100 mg.

39. Celiprolol hydrochloride for the use of any one of 35 to 38 above, wherein at the end of the titration period, celiprolol hydrochloride is administered at a dose superior to 360 mg/day.

40. Celiprolol hydrochloride for the use of any one of 35 to 39 above, wherein at the end of the titration period, celiprolol hydrochloride is administered at a dose of about 400 mg per day.

41. Celiprolol hydrochloride for the use of any one of 35 to 40 above, wherein after the three-month titration period, one or two additional dose increases are performed to reach a daily dose of about 500 mg or about 600 mg.

42. Celiprolol hydrochloride for the use of any of one 35 to 41 above, wherein the patient is 15-years old or older.

43. Celiprolol hydrochloride for the use of any one of 35 to 41 above, wherein the treatment with celiprolol hydrochloride is initiated as soon as vascular EDS is diagnosed, or when the patient is 10 years old.

44. Celiprolol hydrochloride for the use of any one of 35 to 43 above, wherein the patient is not co-administered itraconazole.

45. Celiprolol hydrochloride for use in treating vascular Ehlers-Danlos syndrome in a patient that is receiving a 360 to 440 mg daily dose of celiprolol hydrochloride and having a need to cease the treatment, wherein the daily dose of celiprolol hydrochloride is reduced for no more than about 100 mg a day.

46. Celiprolol hydrochloride for use of 45 above, wherein the reduction continues for at least 5 days.

47. Celiprolol hydrochloride for use of 46 above, wherein the reduction continues for at least 7 days.

48. Celiprolol hydrochloride for use of 46 above, wherein the reduction continues for at least 10 days.

Other characteristics of the disclosure will also become apparent in the course of the description which follows of the biological assays which have been performed in the framework of the disclosure and which provide it with the required experimental support, without limiting its scope.

EXAMPLES

In order to further characterize the protective effect of celiprolol in vEDS, the inventors performed a follow-up of a large patient cohort over a 17-year period. The following are examples of methods of the disclosure. It is understood that various other embodiments may be practiced, given the general description provided above.

Methodology

Patients

All patients with clinically and molecularly diagnosed vEDS that were actively followed clinically in the French National Referral Centre for Rare Vascular Diseases (HEGP, AP-HP, Paris, France) between January 2000 and March 2017 were screened for participation. During the initial evaluation of the first affected family member seeking medical attention for symptoms related to vEDS (index case), familial medical history was recorded and investigation performed in the first-degree relatives whenever possible. A dedicated database for vEDS was created at our institution in 2011. All relevant clinical data of every vEDS patient followed by our centre was entered into this database retrospectively from the year 2000 until 2011, and prospectively thereafter until Mar. 15, 2017. The database contains all available medical history related to the pathology before the initial work-up and obtained during the follow-up either through systematic visits or those caused by a new clinical event. Thus, the occurrence of any acute arterial, gastrointestinal, pulmonary and other vEDS-related events was systematically recorded. In case of death during follow-up, the time and cause of death were entered into the database. This study was formally approved by the IDF ethics committee (IRB registration #00001072) and the database was held in compliance with French legislation on patient privacy.

Study Design

All vEDS patients benefited from standardized whole body arterial monitoring by Doppler Ultrasound (DUS) and CT angiogram and/or MRA. Such investigations were performed at baseline (initial assessment at molecular diagnosis) and was repeated every 12 to 15 months in asymptomatic patients. For arterial events that occurred before molecular diagnosis, location of arterial segments was retrieved from hospitalization and imaging reports or examinations, when available. In case of an acute arterial event, symptomatic arterial beds/segments were monitored by any necessary diagnostic and therapeutic means (CT-angiogram, DUS, angiography in case of embolization). Between routine surveillance work-up, patients were seen for outpatient visits every 6 to 9 months, except during molecular diagnosis and celiprolol dose up-titration. For optimized management of arterial, gastrointestinal, and pulmonary emergencies, patients were given direct access to the medical team of our centre.

Administration of Celiprolol

Since the publication of the BBest trial in 2011, all included patients followed by our centre and not already treated with celiprolol were offered to switch to celiprolol. Patients who were not part of the trial and who were diagnosed during or since the termination of the BBest trial were treated with celiprolol starting at molecular diagnosis. Initial dosing of celiprolol was 100 mg once daily and increased by 100 mg/day every month over a 3-month period to reach the dose of 400 mg/day (200 mg twice daily) (celiprolol hydrochloride). In case of signs of intolerance (fatigue, dizziness) during up-titration or follow-up, the dose of celiprolol was reduced by 100 mg/day until the highest tolerated dose was reached. Dose adjustments were made whenever necessary throughout the patient's follow-up if intolerance was suspected. In accordance with the treatment protocol of the BBEST trial, patients were up-titrated to a maximum dose of 200 mg twice daily.

Adherence to medication was verified by open interview of the patients at each follow-up visit. Low medication adherence was considered if patients admitted to not taking their medication regularly at any moment of their follow-up. Patients were considered intolerant to celiprolol in case of refusal to follow the prescription even at a minimum dose of 100 mg/day. Patients taking another beta-blocker were offered to switch to celiprolol but this change was not mandatory, especially if patients had been clinically silent until molecular diagnosis while under another betablocker. If an acute arterial event occurred, patients were once again offered to switch to celiprolol. To reach significant numbers to allow comparative analysis, intolerant patients, patients not taking celiprolol, patients taking another betablocker and non-adherent patients were merged into one group further referred to as "not treated".

Arterial Progression

In order to assess arterial morbidity over a long timeline in patients with different follow-up periods, an empirical arterial score was designed for each subject. Arterial accidents were weighted as follows: 10 points for arterial ruptures located in the abdomen/thorax/head/neck or for carotid-cavernous fistulas; 5 points for lower or upper limb arterial ruptures as well as arterio-venous fistulas, 2 points for symptomatic dissections (any location) and 1 point for silent dissections, aneurysms and false-aneurysms when diagnosed during an acute arterial event. The arterial progression score was calculated for each patient at the time of the initial work-up hence quantifying history of symptomatic arterial accidents at baseline. Clinical arterial events occurring thereafter (i.e. during the follow-up until the end of the study) were then added to the initial score. According to their initial score, patients were divided into 4 levels of clinical progression: very low (score 0-1 point); low (score 2-8 points); medium (score 9-19 points) or high (score 20 points).

Genetics

After initial referral and clinical assessment, patients underwent molecular testing for a COL3A1 variant after written informed consent. The modalities of molecular analysis have been reported in detail previously (Frank M et al. Eur J Hum Genet. 2015; December; 23(12):1657-64). After identification of a pathogenic mutation, patients were staged by type of variant, with respect to expected differences in outcomes. For this study, patients were divided into four groups: patients with a glycine substitution within the triple helix (Group I), patients with splice-site variants (Group II), patients with variants leading to haplo-insufficiency (Group III), and patients with variants located in portions of COL3A1 encoding for the C- and N-Terminal parts of the protein, as well as non-Glycine substitutions within the triple helix (Group IV). For this report, we did not take into consideration the few patients with Group IV variants, since their causality is only suggested and has not been definitively proven.

Statistical Analysis

Quantitative data were expressed as number, median, first and third quartiles; qualitative data were expressed as number and percentage. Qualitative parameters were compared with the Chi-square test or Fisher's exact test as appropriate. Quantitative variables were compared with the Wilcoxon-Mann-Whitney or the Kruskal Wallis tests, as appropriate. Associations between survival or time until event and compliant patients were examined using the Kaplan-Meier curve and Log rank test was used to assess the significance. A Cox proportional hazards model was used to evaluate predictive factors. Data were censored if a patient was still alive (or without event) at the end date of data collection (Mar. 15, 2017). All tests were two-sided, and significance was assumed at $p<0.05$. Statistical analyses were done with SAS software version 9.2 (Institute INC, Cary, N.C., USA) and XLSTAT software version 2016.4 (Addinsoft).

Results

Patients

Between January 2000 and March 2017, n=144 patients with molecularly confirmed vascular EDS were found eligible for participation in this study (FIG. 1). A majority (n=90) had glycine missense mutations (Group I), others had splice variants (n=42, Group II) and n=12 had variants leading to haplo-insufficiency (Group III). Patients were followed for a median duration of 5.30 [3.20; 8.45] years. The longest documented follow-up was 20 years, and half of patients (55.6%) had a follow up >5 years. The characteristics of patients according to treatment at baseline are reported in Table 1. As expected, patients were young (34.5 years at diagnosis) had low body mass index (21.2 $Kg/m^2$) and normal blood pressure values. There was a slight female predominance (60.4%). Almost ⅔ of the patients were index cases typically referred for diagnostic work-up due to unusual vascular fragility. Thus, overall, many patients (n=98, 68.1%) had experienced a disease related event before follow-up. More than half (51.4%) had an arterial event as the first disease-related complication, whereas a first digestive rupture had occurred in 22.9% of the cases, pneumothorax or hemopneumothorax being less frequent (n=15; 10.4%) (Table 1). There was no difference in the initial characteristics of the patients depending on the type of medical intervention, except those (n=8, age at molecular diagnosis 55.5 years) who were left on medications other than celiprolol, mainly because of clinical stability on combination drugs at the time of inclusion in the cohort study.

TABLE 1

Baseline characteristics of n = 144 patients with vascular EDS according to treatment.

| Patient's characteristics N (%) or median [IQR] | N = 144 All patients | N = 104 Celiprolol alone | N = 26 Celiprolol + Another drug |
|---|---|---|---|
| Sex | | | |
| Female | 87 (60.4) | 66 (63.5) | 12 (46.2) |
| Male | 57 (39.6) | 38 (36.5) | 14 (53.8) |
| Age at molecular diagnosis | 34.5 [25.0; 42.5] | 32.5 [24.0; 40.5] | 38.0 [33.0; 45.0] |
| Status | | | |
| Index case | 91 (63.2) | 67 (64.4) | 19 (73.1) |
| Relative | 53 (36.8) | 37 (35.6) | 7 (26.9) |
| Type of variant | | | |
| Group I | 90 (62.5) | 58 (55.8) | 22 (84.6) |
| Group III | 42 (29.2) | 36 (34.6) | 4 (15.4) |
| Group III | 12 (8.33) | 10 (9.62) | 0 |

TABLE 1-continued

Baseline characteristics of n = 144 patients with vascular EDS according to treatment.

| Baseline characteristics | | | |
|---|---|---|---|
| BMI (kg/m$^2$) | 21.2 [19.0; 23.7] | 21.0 [19.0; 23.0] | 22.9 [20.5; 26.1] |
| SBP (mmHg) | 114.0 [106.0; 123.0] | 113.0 [105.0; 121.0] | 120.0 [112.0; 126.0] |
| DBP (mmHg) | 70.0 [65.0; 78.0] | 70.0 [64.0; 76.0] | 74.0 [65.0; 83.0] |
| Heart rate (bpm) | 72.0 [64.0; 81.5] | 73.0 [65.0; 83.0] | 71.0 [65.0; 79.0] |
| Medical history (Patients with at least one event) Overall | | | |
| n patients | 98 (68.1) | 69 (66.3) | 21 (80.8) |
| n events | 227 | 162 | 47 |
| Arterial events | | | |
| n patients | 74 (51.4) | 50 (48.1) | 19 (73.1) |
| n events | 156 | 105 | 39 |
| Gastrointestinal events | | | |
| n patients | 33 (22.9) | 27 (26.0) | 3 (11.5) |
| n events | 47 | 39 | 4 |
| Pulmonary events | | | |
| n patients | 15 (10.4) | 11 (10.6) | 2 (7.69) |
| n events | 24 | 18 | 4 |
| Follow-up length (year) | 5.30 [3.20; 8.45] | 5.15 [3.10; 8.35] | 7.15 [4.90; 11.3] |

| Patient's characteristics N (%) or median [IQR] | N = 8 Other drugs | N = 6 No treatment | P value |
|---|---|---|---|
| Sex | | | 0.4201 |
| Female | 5 (62.5) | 4 (66.7) | |
| Male | 3 (37.5) | 2 (33.3) | |
| Age at molecular diagnosis | 55.5 [41.0; 67.5] | 31.0 [15.0; 51.0] | 0.0005 |
| Status | | | 0.0632 |
| Index case | 4 (50.0) | 1 (16.7) | |
| Relative | 4 (50.0) | 5 (83.3) | |
| Type of variant | | | 0.0491 |
| Group I | 5 (62.5) | 5 (83.3) | |
| Group III | 1 (12.5) | 1 (16.7) | |
| Group III | 2 (25.0) | 0 | |
| Baseline characteristics | | | |
| BMI (kg/m$^2$) | 22.6 [17.3; 28.4] | 20.6 [19.0; 22.5] | 0.2415 |
| SBP (mmHg) | 112.5 [107.0; 131.0] | 113.5 [104.0; 120.0] | 0.2145 |
| DBP (mmHg) | 75.0 [68.0; 85.0] | 69.0 [68.0; 76.0] | 0.2837 |
| Heart rate (bpm) | 64.5 [57.5; 69.0] | 65.5 [59.0; 76.0] | 0.0920 |
| Medical history (Patients with at least one event) Overall | | | |
| n patients | 6 (75) | 2 (33.3) | 0.1319 |
| n events | 14 | 4 | |
| Arterial events | | | |
| n patients | 3 (37.5) | 2 (33.3) | 0.0752 |
| n events | 9 | 3 | |
| Gastrointestinal events | | | |
| n patients | 3 (37.5) | 0 | 0.1603 |
| n events | 4 | 0 | |
| Pulmonary events | | | |
| n patients | 1 (12.5) | 1 (16.7) | 0.7937 |
| n events | 1 | 1 | |
| Follow-up length (year) | 3.55 [2.90; 6.05] | 4.30 [1.30; 5.20] | 0.0123 |

Chi-square test or Fisher exact test($^f$) for qualitative variables and Mann-Whitney test for quantitative variables.
Abbreviations: BMI: body mass index; DBP: diastolic blood pressure; IQR: interquartile range; SBP: systolic blood pressure
Group I: Glycine missense variants; Group II: splice-site variants, insertions-deletions, duplications; Group III: variants leading to haploinsufficiency.

Medical Intervention

At the initial work-up, 50% of the patients were not treated regularly and only 33.3% were taking celiprolol. Other cardiovascular drugs were also being taken at baseline, predominantly beta-blockers (12.5%) and/or angiotensin II receptor blockers (ARBs) or angiotensin-converting enzyme inhibitors (ACEIs) (6.9%). By the end of the study period, almost all patients (90.3%) were treated with celiprolol alone or in combination. The proportion of patients taking ACEIs/ARBs increased with age to a maximum of 20.1%. Common indications were arterial hypertension and renal ischemia with reno-vascular hypertension. Once the maximum tolerated dose of celiprolol was reached, n=90 (62.5%) patients remained at identical dosage throughout their respective follow-up periods. Further dose increase was possible in n=32 (22.2%) of patients. Only n=5 (3.47%) patients required dose reduction due to fatigue and/or dizziness.

For patients taking celiprolol, the median treatment duration for all patients was 5.2 [3.0; 7.3] years (min-max 0.5-13.5). During their respective follow-up, n=120/144 (83.3%) patients were considered adherent to celiprolol at either 400 mg/day (n=92; 63.9%), or at doses <400 mg/day (n=28; 19.4%). The median dose of celiprolol throughout follow-up was 400 mg/day [333; 400] in patients at full dose, and 217 mg/day [200; 300] in patients at lower doses. A minority of patients (n=14; 9.7%) were reported non-adherent at some point of their follow-up, n=7 (4.9%) had another beta-blocker, and n=2 (1.4%) declared themselves as intolerant to celiprolol or refused to take it in fear of intolerance. Median dose of celiprolol in non-adherent patients was lower than in adherent patients: 200 mg/day [200; 300] versus 378 mg/day [233; 400], respectively.

Figure 3A:
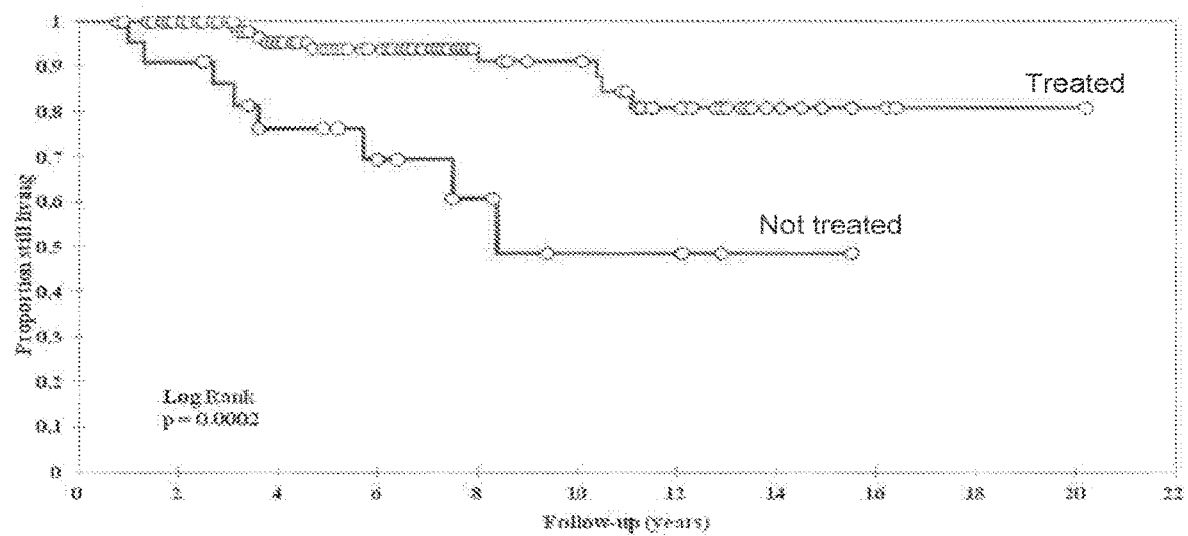
FIG. 3A. Survival according to celiprolol treatment (treated patients versus not treated patients (i.e. no treatment, non-adherent, intolerant to celiprolol, celiprolol not started and patients taking another drug than celiprolol): At the end of follow-up, survival was 80.7%, 95% CI [67.8%-93.6%] in those treated with celiprolol versus 48.5%, 95% CI [19.7%-77.4%] in those not treated. Log Rank: Treated (n=110) versus Not Treated (n=22), p=0.0002.
Figure 3B:
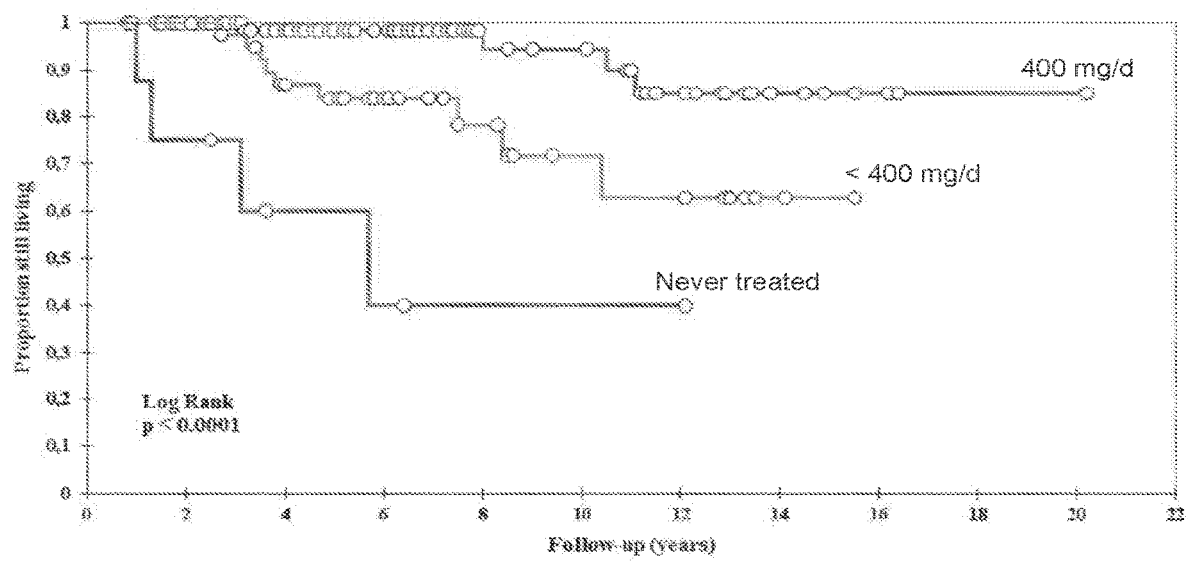
FIG. 3B. Survival according to daily dose of celiprolol: At the end of follow-up, survival was 85%, 95% CI [70.5%-99.5%] in those patients treated by celiprolol 400 mg/day, 62.8%, 95% CI [39.7%-86.0%] in those taking celiprolol 100-300 mg/day, 40.0% 95% CI [0.2%-79.8%] in the non-treated group (B). Log rank survival analysis between the 3 groups: p<0.0001.

Comparison of dead patients with survivors demonstrated a significant association between celiprolol and survival (Table 2). Because of the influence of the type of mutation, we restricted our analysis to the n=132 patients with the Group I and II mutations, those known as the most severe forms of the disease. This selection was also justified by the high number of relatives in the group III (10 relatives vs 2 index cases), their milder phenotype and their shorter average duration of follow-up (3.2 vs 6.3 years, p<0.01). On this more homogeneous group of n=132 patients, those not treated with celiprolol, had a significantly worse outcome than treated patients (FIG. 3A): survival was 80.7%, 95% CI [67.8%-93.6%] in those treated with celiprolol versus 48.5%, 95% CI [19.7%-77.4%] in those not treated (p<0.001). Moreover, in adherent patients, survival was significantly improved in patients taking celiprolol at 400 mg/day, when compared to patients with lower doses or to patients having never been treated with celiprolol (FIG. 3B). Independent predictors of survival determined by a Cox stepwise hazards model were an age at molecular diagnosis <34 years (p<0.0001), treatment duration with celiprolol >6 years (p=0.01) and celiprolol intake at 400 mg/d (p=0.01) (Table 3).

TABLE 2

Characteristics of patients who died during follow-up compared to surviving patients.

| Patients | | Deceased patients N = 17 N (%) or median [Q1; Q3] | Alive N = 127 N (%) or median [Q1; Q3] | P value |
|---|---|---|---|---|
| Sex | Male | 9 (52.9%) | 48 (37.8%) | 0.2304 |
| | Female | 8 (47.1%) | 79 (62.2%) | |
| Age at the beginning of the follow-up | | 28.0 [21.0; 38.0] | 35.0 [26.0; 43.0] | 0.0765 |
| Age at death or at the last-follow-up | | 35.0 [26.0; 41.0] | 41.0 [33.0; 50.0] | 0.0496 |
| Status | Index case | 13 (76.5%) | 78 (61.4%) | 0.2268 |
| | Relative | 4 (23.5%) | 49 (38.6%) | |
| Type of variant | Group I | 13 (76.5%) | 77 (60.6%) | 0.5802 |
| | Group II | 4 (23.5%) | 38 (29.9%) | |
| | Group III | 0 | 12 (9.45%) | |
| Treatment with celiprolol | Yes | 9 (52.9%) | 111 (87.4%) | 0.0017 $^f$ |
| | No | 8 (47.1%) | 16 (12.6%) | |

Chi square test or Fisher exact test($^f$) for qualitative variables and Mann-Whitney test for quantitative variables. Bold value indicates p < 0.05.

Patient Survival

During the 17-year timeframe of the study, n=17 (11.8%) patients died at a relatively young age (35[26-41]). Arterial rupture was the most common cause of death (n=12, 70.6%), followed by bowel perforation (n=2, 11.8%), the three remaining deaths not being related to vEDS.

Figure 2A:
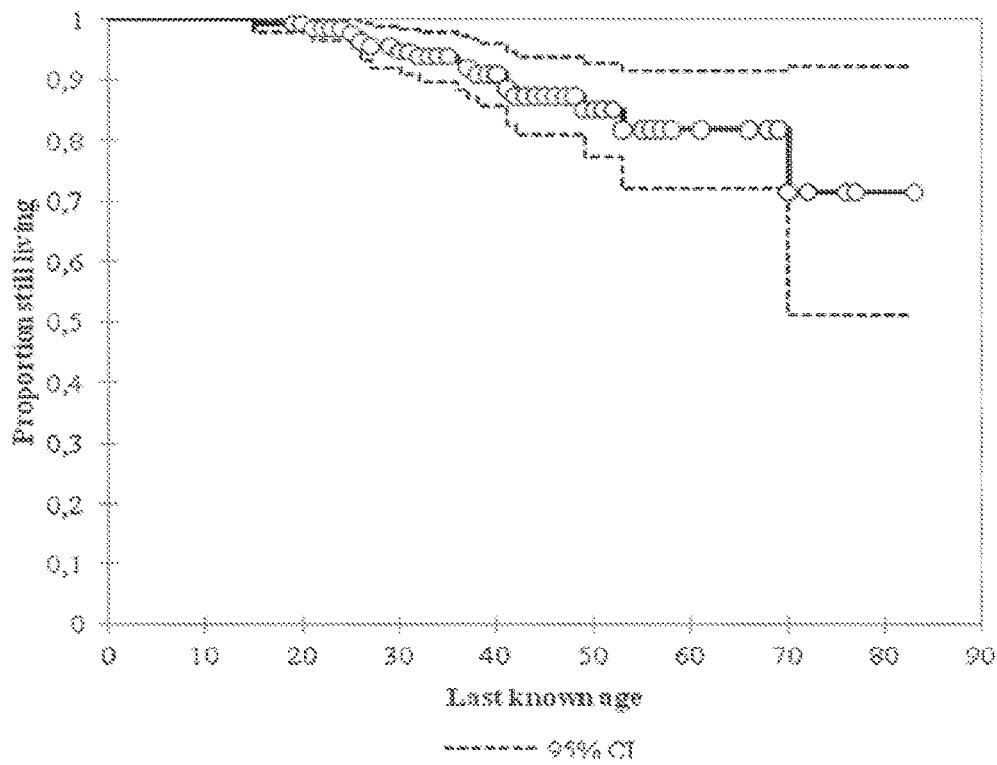
FIG. 2A. Overall patient survival: 71.6%; 95% CI [51.0%; 92.1%].
Figure 2B:
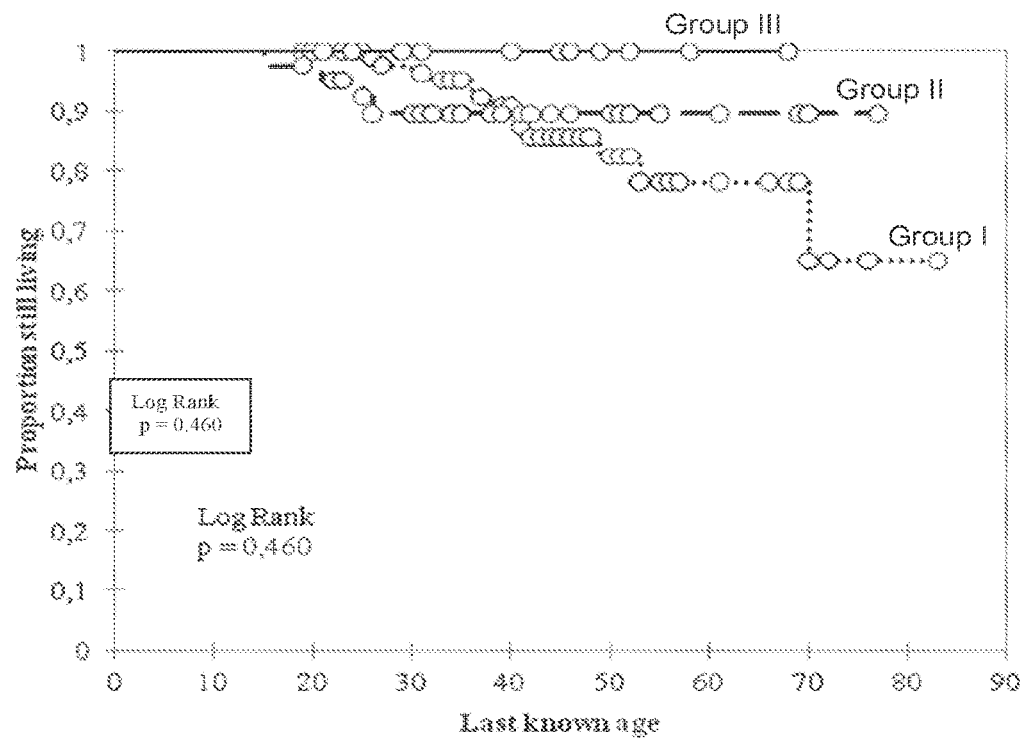
FIG. 2B. Survival according to the type of variant (Group I versus Group II versus Group III). Group I: 65.1%; 95% CI [39.5%; 90.7%] versus Group II: 89.6%; 95% CI [79.9%; 99.3%] versus Group III: 100%.

Survival of patients was respectively 98.6% at 1 year, 92% at 5 years, and 82.7% at 10 years of follow-up. Overall patient survival was 71.6% 95% CI [51.0%-92.1%] (FIG. 2A). Due to the low number of deaths, a median age of survival could not be determined. Patient survival did not significantly differ between groups of mutations. Notably, no death occurred in patients of Group III (haplo-insufficiency) (FIG. 2B). Index patients were consistently more symptomatic over time than relatives.

TABLE 3

Multivariate survival analysis adjusted for prognostic factors (Cox's model) in n = 132 patients (Groups I and II).

| | Hazard ratio | [95% CI] | P value |
|---|---|---|---|
| Factor | | | |
| Status | | | |
| Relative/Index | 0.145 | [0.030; 0.700] | 0.0162 |
| Gender | | | |
| Male/Female | 0.920 | [0.260; 3.251] | 0.8973 |
| Age at diagnosis | | | |
| ≥41 years/<25 years | 0.001 | [0.0001; 0.022] | <0.0001 |
| 34-41 years/<25 years | 0.001 | [0.0001; 0.029] | <0.0001 |
| 25-34 years/<25 years | 0.039 | [0.004; 0.345] | 0.0036 |

TABLE 3-continued

Multivariate survival analysis adjusted for prognostic factors
(Cox's model) in n = 132 patients (Groups I and II).

| | Hazard ratio | [95% CI] | P value |
|---|---|---|---|
| Treatment duration | | | |
| ≥6 years/<6 years Celiprolol treatment | 0.058 | [0.010; 0.352] | 0.0020 |
| Full dose/No | 0.048 | [0.009; 0.249] | 0.0003 |
| Half dose/No | 0.303 | [0.071; 1.292] | 0.1065 |
| Type of variant | | | |
| Group II/Group I | 0.459 | [0.098; 2.148] | 0.3224 |
| Stepwise method | | | |
| Status | | | |
| Relative/Index | 0.196 | [0.047; 0.814] | 0.0249 |
| Age at diagnosis | | | |
| ≥41 years/<25 years | 0.001 | [0.0001; 0.024] | <0.0001 |
| 34-41 years/<25 years | 0.001 | [0.0001; 0.034] | <0.0001 |
| 25-34 years/<25 years | 0.046 | [0.005; 0.405] | 0.0056 |
| Treatment duration | | | |
| ≥6 years/<6 years Celiprolol treatment | 0.058 | [0.011; 0.314] | 0.0010 |
| Full dose/No | 0.060 | [0.013; 0.277] | 0.0003 |
| Half dose/No | 0.305 | [0.078; 1.184] | 0.0862 |

Arterial Events

At the initial work-up, 74 out of the 144 patients (51.4%), had a history of acute arterial event or arterial lesions detected at CTA and/or DUS, at a median age of 33.0 years ([27.0; 40.5]; min-max.: 13-70) (Table 1). Almost one-fifth (22.7%) reported two symptomatic arterial events and n=11 (8.3%) patients presented with a third arterial event prior to diagnosis. As a consequence of the recruitment bias mainly based on initial symptoms or complications for patients with vascular EDS, index cases had a higher history of previous medical events than their first-degree relatives (82.4% vs 43.4%, p<0.0001) in spite of their younger age (33 vs. 41 years, p=0.001).

Combined with secondary arterial defects identified in the context of these symptomatic arterial events, a total of n=398 arterial lesions were identified in n=74 patients. The most common were dissections (70.1%), followed by aneurysms and false aneurysms (20.4%), arterial ruptures (6.0%), and direct spontaneous carotid cavernous fistula (2.5%). The most common locations of arterial defects were the abdominal aorta and its branches (digestive and renal arteries) (37.2%), carotid and vertebral arteries (29.4%), and iliac and femoral arteries (26.6%). Uncommon locations were the thoracic aorta, coronary arteries, and peripheral arteries of the upper and lower limbs.

Figure 4:
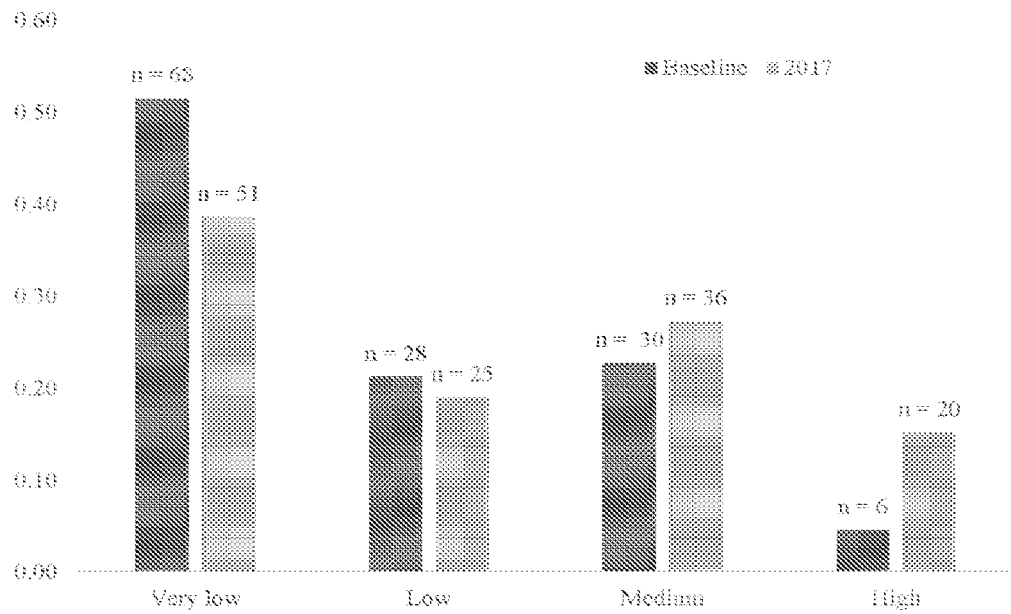
FIG. 4: Evolution of the clinical arterial score throughout follow-up.

During follow-up, all patients of Group III remained clinically silent. Arterial accidents occurred in patients of Groups I and II, totaling n=237 new arterial defects in n=66 patients, 87 of them being symptomatic in n=43 patients. Among these, 15 led to death, others were medically or surgically treated. To evaluate qualitatively and quantitatively the severity of arterial lesions, we designed an arterial score taking into consideration the type, number and locations of arterial lesions observed on CTA and/or DUS (see methods). The distribution of this arterial score showed that most patients (73%) were in the lower group at baseline (FIG. 4). At the end of the follow-up a majority of patients remained in their respective progression groups: very low 75% ($^{51}/_{68}$), low 71.4% ($^{20}/_{28}$) and medium 70% ($^{20}/_{28}$), indicating clinical stability in more than two thirds of patients.

Effect of Celiprolol on the Incidence of Acute Arterial Events

A total of 87 new arterial events (symptomatic) occurred in 43 patients, i.e. less than 30% of patients. For each of these patients, we observed 1 to 5 new arterial events, with an average of 1.7±1.02 events over a 5.3 years follow-up period. At the time of the occurrence of the new arterial event, 33 out of these 43 patients were treated by celiprolol alone (n=28) or in combination with another drug (n=5), proportions which were not different from that of the entire group (104/144 and $^{26}/_{104}$, respectively). It was not possible to assess if the drug had an effect on the delay these arterial events occurred and/or if it was associated with a decreased severity or different locations. The cumulative incidence of a first and second new arterial event during follow-up was 56.8% (95% CI [45.7; 70.5]) and 29.8% (95% CI [17.6; 50.4]), respectively. The mean age of occurrence of this first and second new arterial event was 37 (95% CI[35; 42]) years and 48 (95% CI[42; 65]) years, respectively, without identifiable effect of celiprolol.

Figure 5A:
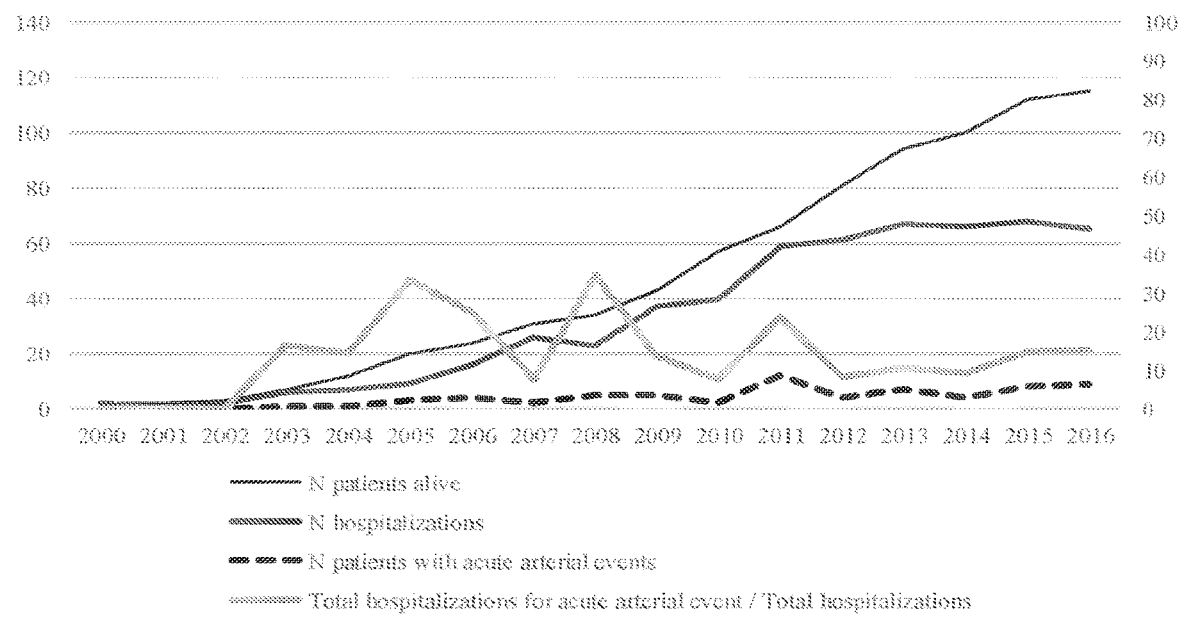
FIG. 5A. Rate of patients and hospitalizations during the study.
Figure 5B:
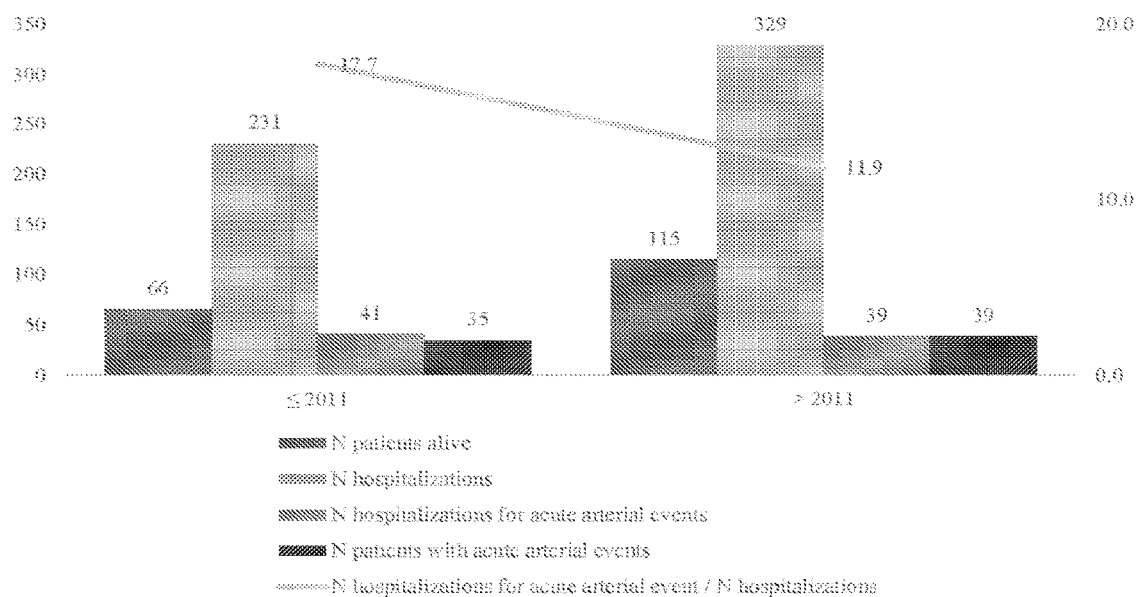
FIG. 5B. Rate of hospitalizations for acute arterial event before and after the systematic introduction of celiprolol.

We then looked at the cumulative number of hospitalizations during the complete survey. The hospitalisations for both symptomatic arterial accidents and arterial monitoring in clinically silent patients, paralleled the total number of patients (FIG. 5A). Interestingly, despite no change in patient monitoring standards, the hospitalization rates stabilized with the generalized prescription of celiprolol starting 2011 despite a constant increase of patients followed by our centre. Notably, total number of hospitalizations for acute arterial accidents decreased, as well as recurrent hospitalizations of patients with repeated symptomatic arterial accidents. We observed a statistically significant difference between the rate of hospitalizations for acute arterial event before and after 2011 (OR 1.72, 95% CI [1.0670-2.7620], p=0.0257), suggesting a positive effect of celiprolol on the occurrence and/or severity of these new arterial events (FIG. 5B).

The data show that patients treated with celiprolol had a better survival than others. The observed reduction in mortality was dose-dependent, 400 mg/day of celiprolol HCl is better than a smaller dose administering, and full doses of celiprolol to vEDS patients with shorter up-titration and dose escalation periods of about three months provided improved treatment benefits, such as overall survival, without significant increase in celiprolol intolerance and side effects.

Although the foregoing disclosure has been described in some detail by way of illustration and example for purposes of clarity of understanding, the descriptions and examples should not be construed as limiting the scope of the disclosure. The disclosure of all patent and scientific literature cited herein are expressly incorporated in their entirety by reference.

The invention claimed is:

1. A method for treating vascular Ehlers-Danlos syndrome, comprising administering to a patient in need thereof an initial daily dose of about 91.25 mg celiprolol, or an equivalent amount of a pharmaceutically acceptable salt thereof, for about 1 month, followed by administering to the patient a second daily dose of about 182.5 mg celiprolol, or an equivalent amount of a pharmaceutically acceptable salt thereof, for about 1 month, followed by administering to the patient a third daily dose of about 273.75 mg celiprolol, or an equivalent amount of a pharmaceutically acceptable salt thereof, for about 1 month, followed by administering to the patient a fourth daily dose of about 365 mg celiprolol, or an equivalent amount of a pharmaceutically acceptable salt thereof.

2. The method of claim 1, wherein the second daily dose is administered twice daily.

3. The method of claim 2, wherein the fourth daily dose is administered twice daily.

4. The method of claim 1, wherein the fourth daily dose is administered for at least 1 year.

5. The method of claim 1, wherein the fourth daily dose is administered for at least 5 years.

6. The method of claim 1, wherein the patient is 15-years old or older.

7. The method of claim 1, wherein the treatment is initiated as soon as vascular EDS is diagnosed, or when the patient is 10 years old.

8. A method for treating vascular Ehlers-Danlos syndrome, comprising administering to a patient in need thereof an initial daily dose of about 100 mg celiprolol hydrochloride for about 1 month, followed by administering to the patient a second daily dose of about 200 mg celiprolol hydrochloride for about 1 month, followed by administering to the patient a third daily dose of about 300 mg celiprolol hydrochloride for about 1 month, followed by administering to the patient a fourth daily dose of about 400 mg celiprolol hydrochloride.

9. The method of claim 8, wherein the initial daily dose is administered at about 100 mg once daily.

10. The method of claim 8, wherein the second daily dose is administered at about 100 mg twice daily.

11. The method of claim 8, wherein the fourth daily dose is administered at about 200 mg twice daily.

12. The method of claim 8, wherein the fourth daily dose is administered for at least 1 year.

13. The method of claim 8, wherein the fourth daily dose is administered for at least 5 years.

14. The method of claim 8, wherein the patient is 15-years old or older.

15. The method of claim 8, wherein the treatment is initiated as soon as vascular EDS is diagnosed, or when the patient is 10 years old.

* * * * *